(12) United States Patent
Masuda et al.

(10) Patent No.: US 7,973,199 B2
(45) Date of Patent: Jul. 5, 2011

(54) PROCESS FOR PRODUCING ACETONE FROM BIOETHANOL

(75) Inventors: Takao Masuda, Sapporo (JP); Teruoki Tago, Sapporo (JP); Tetusya Yanase, Tokyo (JP); Hirokazu Tsuboi, Tokyo (JP)

(73) Assignees: Metawater Co., Ltd., Tokyo (JP); National University Corporation Hokkaido University, Sapporo-shi Hokkaido (JP)

( * ) Notice: Subject to any disclaimer, the term of this patent is extended or adjusted under 35 U.S.C. 154(b) by 0 days.

(21) Appl. No.: 12/868,018

(22) Filed: Aug. 25, 2010

(65) Prior Publication Data

US 2011/0015445 A1    Jan. 20, 2011

Related U.S. Application Data

(63) Continuation of application No. PCT/JP2009/053830, filed on Mar. 2, 2009.

(30) Foreign Application Priority Data

Mar. 3, 2008  (JP) ................. 2008-051498

(51) Int. Cl.
*C07C 45/29* (2006.01)
*C07C 45/37* (2006.01)

(52) U.S. Cl. ...................................................... 568/403
(58) Field of Classification Search .................. 568/403
See application file for complete search history.

(56) References Cited

FOREIGN PATENT DOCUMENTS

| JP | 59-092023 A1 | 5/1984 |
|---|---|---|
| JP | 07-053433 A1 | 2/1995 |
| JP | 2001-276615 A1 | 10/2001 |
| JP | 2004-208667 A1 | 7/2004 |

OTHER PUBLICATIONS

Nakajima et al. A Highly Active and Highly Selective Oxide Catalyst for the Conversion of Ethanol to Acetone in the Presence of Water Vapour. Journal of Materials Chemistry, 1994, vol. 4 (6), 853-858.*

* cited by examiner

*Primary Examiner* — Sikarl Witherspoon
(74) *Attorney, Agent, or Firm* — Burr & Brown

(57) ABSTRACT

The present invention provides a technique for producing acetone in a high yield from hydrated ethanol derived from biomass, without requiring a large amount of energy. Hydrated ethanol derived from biomass is heated to a reaction temperature of 400° C. or higher in the presence of a Zr—Fe catalyst, thereby producing acetone. The reaction temperature is preferably from 450 to 550° C., and the Zr—Fe catalyst preferably contains 5 to 10% by mass of Zr. The present invention allows purification of hydrated acetone without requiring purification of the hydrated ethanol.

4 Claims, 5 Drawing Sheets

PROCESS FOR PRODUCING ACETONE FROM BIOETHANOL

FIELD OF THE INVENTION

The present invention relates to a process for producing acetone from biomass-derived ethanol. In the present description, biomass-derived ethanol is referred to as bioethanol.

BACKGROUND OF THE INVENTION

For the purpose of preventing the deterioration of the global environment and the exhaustion of oil resources, various techniques for ethanol production from plants or other biomass have been developed, and some are in practical use. For example, Patent Document 1 discloses a process for producing bioethanol, including fermenting a sugar solution, which has been prepared from biomass, into crude ethanol, and distilling the crude ethanol with vapor generated by burning the biomass, thereby obtaining anhydrous ethanol.

Biomass has already absorbed atmospheric $CO_2$ during its generation. Therefore, bioethanol is entirely carbon neutral even if it emits $CO_2$ into the atmosphere during combustion, and thus is expected to contribute to the prevention of global warming. In Japan, bioethanol is used in mixture with automotive gasoline. However, bioethanol emits a large amount of NOx into the exhaust gas and corrodes the automotive engine, so that the maximum rate of addition is limited to 3% by a law. Therefore, Bioethanol is not still effectively used.

In view of the above-described problems, the inventors considered that the conversion of bioethanol into other useful hydrocarbon would promote the utilization of biomass energy and contribute to the resolution of the global environmental problems. The inventors focused attention on the conversion of bioethanol into acetone, which is a ketone. Acetone is known to be converted into gasoline over a zeolite catalyst, and thus is useful for solving the above-described problems.

The Wacker process and the cumene process are generally used for industrial production of acetone. The Wacker process includes direct oxidation of propylene in air over a palladium chloride-copper chloride-based catalyst. The cumene process includes reaction between propylene and benzene over a catalyst of aluminum chloride or phosphoric acid, purifying cumene, and decomposing the cumene after oxidation to produce acetone and phenol. However, these processes use petroleum as a raw material, and thus will not contribute to the resolution of global environmental problems.

As described in Patent Document 1, biomass fermentation requires water, and biomass itself is normally hydrated. Therefore, bioethanol contains a large amount of water. However, the use of bioethanol as a fuel requires high purification. In addition, as shown in FIG. 5, the ethanol fractions in the vapor and liquid phases of ethanol-water mixture are almost the same in the region having a high ethanol concentration, so that a large amount of energy is necessary for increasing the ethanol concentration. According to the process described in Patent Document 1, hydrated ethanol is distilled using water vapor generated by burning biomass, thereby increasing the ethanol concentration. However, the process is still wasteful from the viewpoint of effective utilization of biomass energy. Furthermore, the water-acetone mixture produced according to the present invention has no azeotropic point different from a water-ethanol mixture, and thus allows easier acetone condensation in comparison with the water-ethanol mixture.

Patent Document 1: Japanese Unexamined Patent Application Publication No. 2004-208667

SUMMARY OF THE INVENTION

Problems to be Solved by the Invention

Accordingly, the object of the present invention is to provide a technique for producing acetone in a high yield from hydrated ethanol derived from biomass, without requiring a large amount of energy.

Means for Solving the Problem

In order to achieve the above object, the process for producing acetone from bioethanol of the present invention includes heating hydrated ethanol derived from biomass in the presence of a Zr—Fe catalyst to a reaction temperature of 400° C. or higher, thereby producing acetone. The reaction temperature is preferably from 450 to 550° C., and the Zr—Fe catalyst preferably contains 5 to 10% by mass of Zr. The biomass may be wood-derived or waste-derived biomass.

Advantageous Effect of the Invention

According to the process for producing acetone from bioethanol of the present invention, acetone is directly produced in a high yield of 70% or more, without requiring purification of hydrated ethanol. Therefore, the process does not require a large amount of energy for ethanol purification by removing water. In addition, according to the present invention, acetone is produced from various kinds of biomass such as waste-derived biomass, without depending on petroleum.

Figure 1:
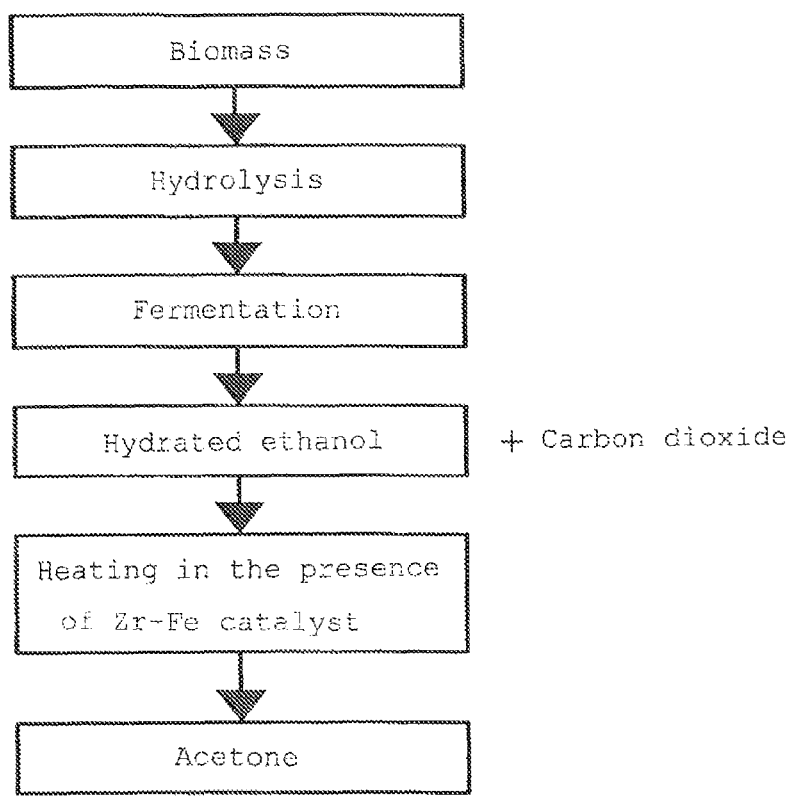
FIG. 1 is a block diagram illustrating the steps of the present invention.

REFERENCE NUMERALS 1 reaction vessel
2 fixed bed
3 electric furnace
4 micro feeder
5 micro feeder
6 capacitor
7 capacitor
8 valve
9 reservoir

DETAILED DESCRIPTION OF THE INVENTION

An embodiment of the present invention is described below.
FIG. 1 is a block diagram illustrating the steps of the present invention, wherein the starting material is biomass. The biomass may be wood-derived biomass such as scrap wood from forestry thinning, waste lumber, sawdust, or paper sludge, or waste-derived biomass such as sewage sludge, kitchen garbage, feces, or wastewater from livestock. The biomass is liquefied, hydrolyzed as necessary, and then subjected to alcoholic fermentation.

When the biomass is wood-derived, it is hydrolyzed into pentose and hexose. The process is due to the hydrolysis of hemicellulose (a polymer of pentose and hexose), which is a major component of wood-derived biomass. For example, rice straw contains about 30% of hemicellulose. Biomass such as sewage sludge, kitchen garbage, or feces may not require hydrolysis, but the biomass may be liquefied through pyrolysis thereby facilitating fermentation.

Subsequently, ethanol is produced by alcoholic fermentation by an yeast in the same manner as in prior art. The ethanol is hydrated ethanol containing water, and secondarily produces carbon dioxide. When the biomass is wood-derived, it theoretically produces 51% by weight of ethanol. In a prior art process, the hydrated ethanol (crude ethanol) thus obtained must be purified using a large amount of energy. In the present invention, the hydrated ethanol can be sent directly to the step of producing acetone.

In the present invention, hydrated ethanol is heated to a temperature of 400° C. or higher in the presence of a Zr—Fe catalyst, thereby producing acetone. The Zr—Fe catalyst used herein is composed of an iron oxide-based catalyst carrying Zr, the Zr content being preferably from 2 to 10% by mass. The iron oxide is hematite. The Zr—Fe catalyst may be produced by a method including immersing an iron oxide-based catalyst in a Zr-containing aqueous solution, filtering the solution to obtain a solid, and then thermally treating the solid in a water vapor atmosphere, or a method including preparing an aqueous solution of Fe and Zr salts, adding an alkali to coprecipitate the salts, and then thermally treating the solid. The iron oxide-based catalyst may contain a small amount of Al to improve the surface area and structural stability.

The Zr—Fe catalyst in the form of grains or a honeycomb is put in a reaction vessel to form a fixed bed, and hydrated ethanol is poured there over. The reaction vessel and the pipe for feeding the hydrated ethanol to the reaction vessel are heated with a heater to achieve a reaction temperature of 400° C. or higher. As shown by the data of the below-described examples, acetone was not produced at a reaction temperature of 300° C., but produced at 400° C. or higher temperatures. The reaction temperature is preferably from 450 to 550° C.

The ethanol concentration in the hydrated ethanol is not necessarily high enough. In the experiment at 400° C., a higher acetone yield was achieved by the lower ethanol concentration. The fact indicates that acetone is produced from hydrated ethanol as it is. When the ethanol concentration in the hydrated ethanol was 50% and the reaction temperature was 500° C., the acetone yield was 70% or more. The produced gas was mostly carbon dioxide, and a trace amount of $CH_3CHO$ was secondarily produced. The acetone-containing gas emitted from the reaction vessel is cooled by a capacitor thereby collecting acetone.

Figure 4:
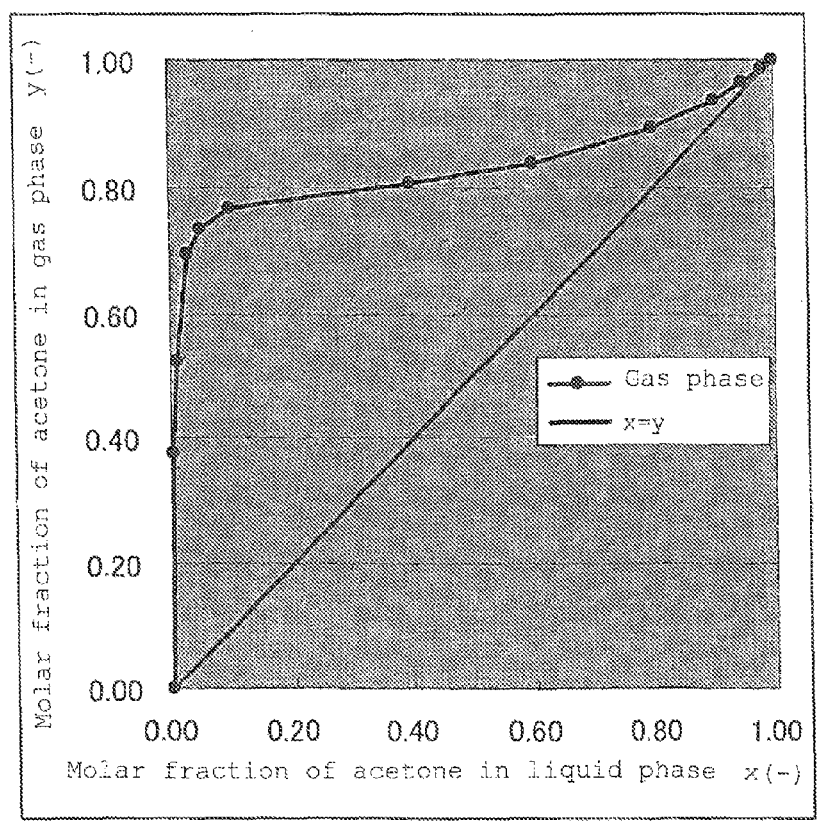
FIG. 4 is a graph of the gas-liquid equilibrium curve of the gas and liquid phases of an acetone/water system.
Figure 5:
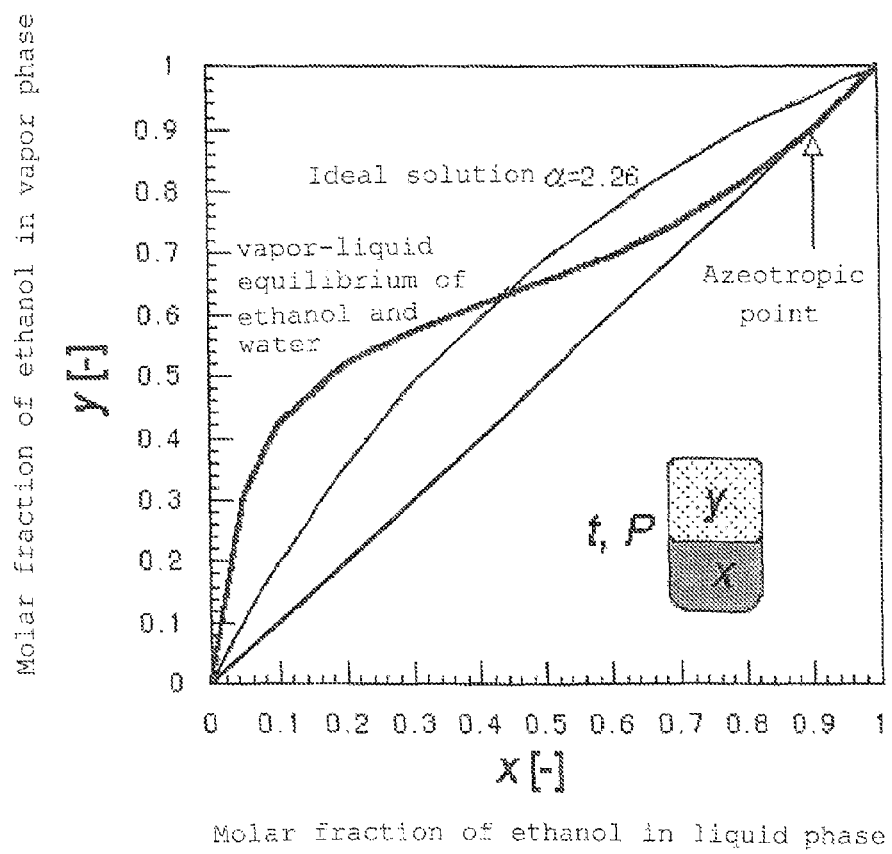
FIG. 5 is a graph of the gas-liquid equilibrium curve of the gas and liquid phases of an ethanol/water system.

In this manner, according to the present invention, acetone is directly produced in a high yield of 70% or more, without requiring purification of the hydrated ethanol. As described above, the graph in FIG. 5 shows that the ethanol fractions in the vapor and liquid phases of ethanol-water mixture are almost the same in the region having a high ethanol concentration, which results in difficulty in purification by distillation. On the other hand, the graph in FIG. 4 indicates that the acetone fraction in the vapor phase of an acetone-water mixture is high even in the region having a high acetone concentration, which facilitates purification by distillation. Therefore, purification of the collected acetone does not require a large amount of energy.

Examples of the present invention are described below.

EXAMPLES

Figure 2:
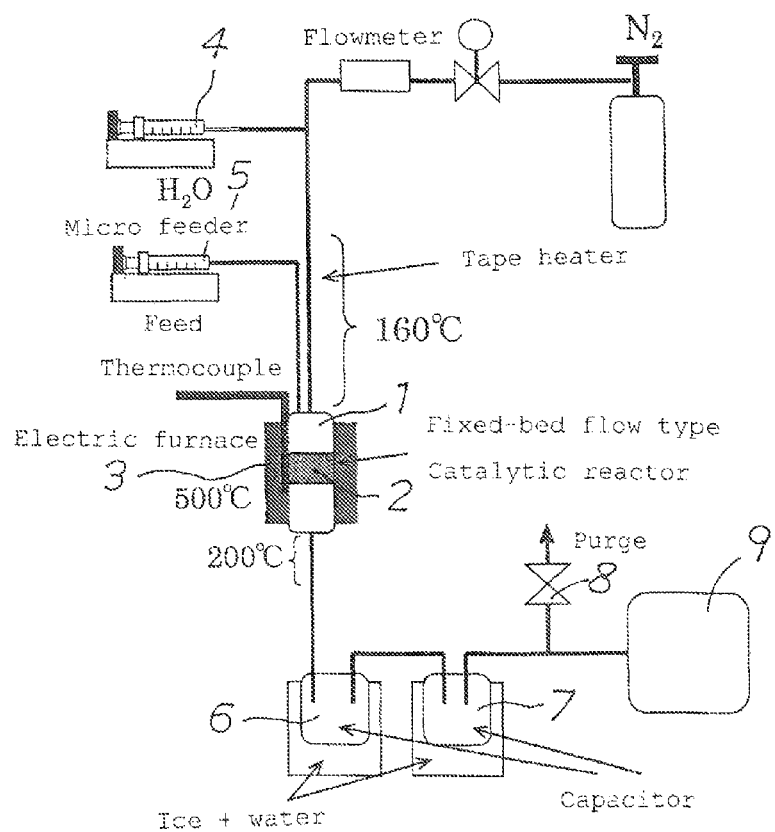
FIG. 2 is a configuration diagram illustrating an apparatus used in the examples.

Using the experimental apparatus shown in FIG. 2, acetone was produced from hydrated ethanol. The reference numeral 1 indicates a reaction vessel, which was filled with grains of a Zr—Fe catalyst, thereby forming a fixed bed 2 which transmits gases and liquids. The Zr—Fe catalyst was an iron oxide-based catalyst carrying 7.7% by weight of Zr. The reaction vessel 1 was put in an electric furnace 3, and heated to 300° C., 400° C., and 500° C.

In order to change the ethanol concentration in the hydrated ethanol, water and pure ethanol (99.5%) were fed to the reaction vessel 1 through micro feeders 4 and 5, respectively. In addition, nitrogen gas was fed to the reaction vessel 1. Each line for feeding them to the reaction vessel 1 was wrapped by a tape heater, and preheated to 160° C. The feed rate was adjusted such that the (catalyst amount)/(aqueous solution feed rate)=1 hour. The gas emitted from the reaction vessel 1 was guided to capacitors 6 and 7 cooled by ice water, and the liquid product containing acetone was collected in a reservoir 9. The nitrogen gas was discharged from a valve 8.

Figure 3:
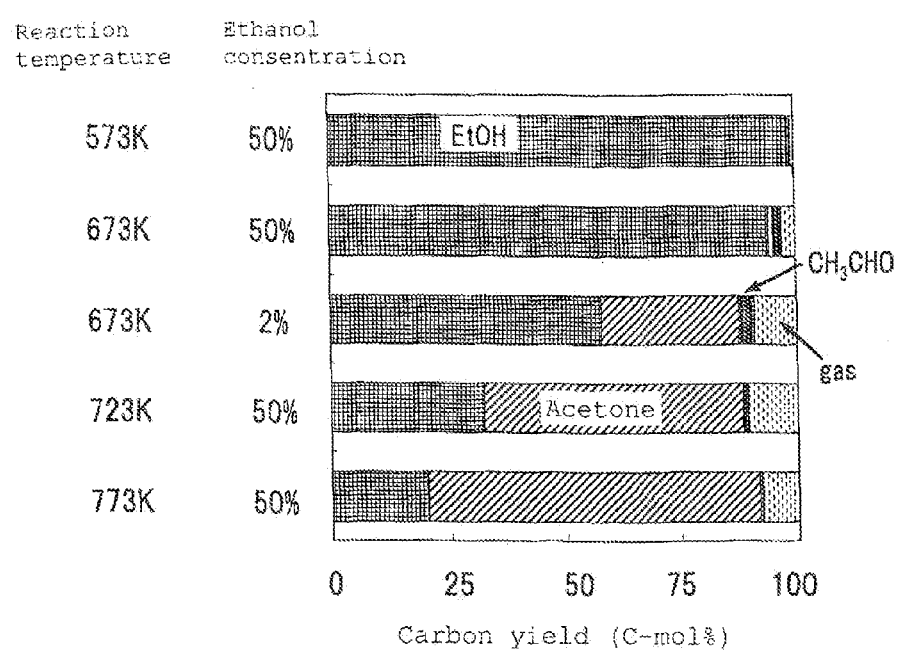
FIG. 3 shows graphs of the product yields in the examples.

The components of the liquid product were analyzed using SHIMADZU GC17 A, and the gas product was analyzed using SHIMADZU GC12A. FIG. 3 shows the product yields at different temperatures and ethanol concentrations. When the reaction temperature was 300° C., the product was ethanol, showing that almost no reaction had occurred. When the reaction temperature was 400° C., almost no reaction had occurred at the ethanol concentration of 50%, but the acetone yield became about 30% at the ethanol concentration of 2%. When the reaction temperature was 450° C., the acetone yield was 60% even at the ethanol concentration of 50%. When the reaction temperature was 500° C., the acetone yield exceeded 70%, indicating that acetone was produced in a high yield. The reaction temperature is preferably from 450 to 550° C., because the thermal stability of the Zr—Fe catalyst decreases when the temperature exceeds about 600° C.

The invention claimed is:

1. A process for producing acetone from bioethanol, comprising heating hydrated ethanol derived from a biomass to a reaction temperature of 400° C. or higher in the presence of a Zr—Fe catalyst, thereby producing acetone.

2. The process for producing acetone from bioethanol of claim 1, wherein the reaction temperature is from 450 to 550° C.

3. The process for producing acetone from bioethanol of claim 1, wherein the Zr—Fe catalyst is composed of iron oxide containing 2 to 10% by mass of Zr.

4. The process for producing acetone from bioethanol of claim 1, wherein the biomass is a wood-derived biomass or a waste-derived biomass.

* * * * *